United States Patent [19]

Cohen et al.

[11] Patent Number: 5,219,837
[45] Date of Patent: Jun. 15, 1993

[54] METHOD OF STIMULATING MYELINATION OF CELLS

[75] Inventors: Jeffrey A. Cohen, Bala Cynwyd; Mark I. Greene, Penn Valley; William V. Williams, Havertown, all of Pa.

[73] Assignee: Trustees of the University of Pennsylvania, Philadelphia, Pa.

[21] Appl. No.: 541,779

[22] Filed: Jun. 21, 1990

[51] Int. Cl.$^5$ .................. A61K 37/02; C07K 7/06; C07K 7/08

[52] U.S. Cl. .......................... 514/12; 514/13; 514/14; 514/15; 514/16; 514/17

[58] Field of Search ..................... 514/12-17

[56] References Cited

U.S. PATENT DOCUMENTS 4,230,696  10/1980  Hashim ................. 514/17
4,615,884  10/1986  Harshman .............. 424/92
5,003,044   3/1991  Hunter et al. ......... 530/330

OTHER PUBLICATIONS

Ventimiglia, R., et al., Proc. Natl. Acad. Sci. USA 84:5073-5077 (1987).

Primary Examiner—Lester L. Lee
Attorney, Agent, or Firm—Woodcock Washburn Kurtz Mackiewicz & Norris

[57] ABSTRACT

The present invention provides methods for treating mammalian diseases and conditions characterized by myelin destruction. The present invention provides methods for inducing myelin formation by myelin forming cells expressing reovirus type 3 receptors comprising administering to such cells an effective amount of a compound bindable with the reovirus type 3 receptor. The compounds for use in the method of the invention preferably comprise antibodies and peptides, more preferably synthetic peptides.

4 Claims, No Drawings

METHOD OF STIMULATING MYELINATION OF CELLS

REFERENCE TO GOVERNMENT GRANTS

The invention disclosed in the present application was supported in part by National Institutes of Health grant NS 01284 to Jeffrey Cohen and National Institutes of Health grant NEI EY 06778 to Mark I. Greene. The United States government has certain rights in the invention.

FIELD OF THE INVENTION

The present invention relates to the field of treatments for demyelination of nerve cells. More particularly the present invention relates to treatment of demyelination injury with peptides bindable with the reovirus type 3 receptor present on the surface of oligodendrocytes.

BACKGROUND OF THE INVENTION

Multiple sclerosis is a highly variable disease for which the cause and pathogenesis remain unknown. No preventive measures or definitive therapies exist. In approximately 60 percent of patients the disease is manifested by exacerbations and remissions. Even in the early stages of disease, clinical recovery from exacerbations may be incomplete leading to accumulation of neurologic deficits. The disease enters a chronic phase and becomes progressively worse over time.

The primary pathology of multiple sclerosis is confined to the central nervous system, where macroscopic lesions ranging from about mm to 4 cm are scattered throughout the white matter. These are known as plaques. Microscopically, the characteristic features are inflammation and myelin damage, with relative sparing of axons. Such observations suggest that the primary site of the pathology is the myelin membrane or the oligodendrocyte.

Due to the lack of effective treatments for multiple sclerosis and the inability to prevent the onset of the disease, treatments to ameliorate or reverse the course of the disease are needed. Accordingly it is an object of the invention to provide methods for stimulating myelination of nerve cells. It is another object of the invention to provide methods for treatment of mammalian diseases characterized by myelin destruction such as multiple sclerosis and after viral infection.

SUMMARY OF THE INVENTION

The present invention provides methods for treating mammalian diseases and conditions characterized by myelin destruction. The present invention provides methods for inducing myelin formation by myelin forming cells expressing reovirus type 3 receptors comprising administering to such cells an effective amount of a compound bindable with the reovirus type 3 receptor. The compounds for use in the method of the invention preferably comprise antibodies and peptides, more preferably synthetic peptides.

In a different aspect of the invention, a method of treating a mammal suffering from myelin destruction of nerves to stimulate remyelination of nerves is provided comprising administering to such a mammal an amount of a compound bindable with the reovirus type 3 receptor present on oligodendrocytes effective to stimulate myelin biosynthesis.

In another aspect of the invention, a method of inducing myelin production in mammals is provided comprising administering to a mammal an amount of a compound bindable with the reovirus type 3 receptor on oligodendrocytes effective to stimulate myelin production.

In a further aspect of the invention, a method of modulating oligodendrocyte differentiation in mammals is provided comprising administering to such cells an effective amount of a compound bindable with the reovirus type 3 receptor expressed on the surface of oligodendrocyte cells.

This invention is more particularly pointed out in the appended claims and described in its preferred embodiments in the following description.

DETAILED DESCRIPTION OF THE INVENTION

Applicants have discovered that peptides bindable with the reovirus type 3 receptor expressed on oligodendrocytes can stimulate oligodendrocyte differentiation and will be useful for treatment of diseases and conditions where destruction of myelin has occurred such as in multiple sclerosis and after viral infection.

Multiple sclerosis lesions contain small amounts of myelin basic protein and increased amounts of proteolytic enzymes. Immunologic staining has shown that the region of decreased myelin-associated glycoprotein extends far beyond the margin of demyelination. The alterations in periaxonal myelin-associated glycoprotein, shown by immunocytochemical staining, have been interpreted as abnormalities of the oligodendrocyte that precede myelin breakdown.

Myelination in the central nervous system (CNS) involves the migration and proliferation of oligodendrocyte precursors, the coordinated synthesis of a variety of myelin components, and morphological adaption of the oligodendrocyte plasma membrane to form the myelin sheath. The regulation of this complex process is poorly understood but is likely to include autonomous mechanisms intrinsic to the oligodendrocyte and its precursors, interactions of cells with the substratum, direct interaction between developing oligodendrocyte and axons and other glia, and the actions of soluble regulatory factors mediated by specific cell-surface receptors. As used herein the term components of myelin biosynthesis includes expression of myelin-specific components such as galactocerebroside, myelin basic protein, peoteolipid protein, myelin assiciated glycoprotein, and cyclic nucleotide phosphohydrolase, as well as the aforementioned compounds themselves. In addition myelination involves wrapping of the axon by an extension of the oligodendrocyte membrane forming the myelin sheath.

Several soluble factors have been identified which appear to be important in the regulation of oligodendrocyte differentiation and function. First, platelet-derived growth factor (PDGF), which is secreted by type-1 astrocytes, is a potent mitogen for 0-2A progenitor cells and prevents their premature differentiation in culture. Second, it appears that the differentiation of 0-2A cells into oligodendrocyte represents a constitutive pathway, initiated coincident with the cessation of progenitor cell proliferation when the cells are cultured in defined medium containing low serum. When cultured in medium containing 10% fetal calf serum (FCS), 0-2A progenitor cells differentiate instead into type 2 astrocytes. A serum component related to ciliary neurotrophic factor is responsible for this activity. Type 1 astrocytes secrete a similar factor. Other soluble factors and hormones proposed to play a role in the regulation of oligodendrocyte development and function include thyroid hormones, insulin and insulin-like growth factors, fibroblast growth factor, and interleukin-2. Finally, oligodendrocyte express several receptors linked to adenylate cyclase, whose activity is modulated by cell-substratum interactions.

The nervous system is an important target tissue of reovirus infection. In rodents reovirus type 1 preferentially infects ependymal cells. Type 3 virus infects neurons and glia. Binding studies using intact virus or antireceptor antibodies have indicated that reovirus serotypes 1 and 3 utilize distinct receptors. Differences in the viral $\sigma$1 protein, which mediates attachment to target cells, and the differential expression of serotype-specific receptor structures on target cells determine the cellular tropism pattern of the virus. Previous studies have demonstrated that in primary cultures of CNS cells, mature neurons, oligodendrocyte, and both type 1 and type 2 astrocytes express immunoreactive reovirus type 3 receptor (Reo3R) but ependymal cells do not. In contrast, ependymal cells express receptors for reovirus type 1 but not type 3.

The reovirus $\sigma$1 outer capsid protein plays a central role in defining the nature of the interaction between virus and the host organism. By serving as the cell attachment protein, the $\sigma$1 protein defines the pathway of Viral spread, the cellular tropism, and the virulence of the virus. The $\sigma$1 protein also is the viral hemagglutinin and is the principal target of both humoral and cell-mediated immune responses to reovirus. Finally, the $\sigma$1 protein mediates reovirus type 3 inhibition of target cell growth and DNA synthesis through its interaction with the cell-surface receptor for reovirus type 3. Studies utilizing primary cultures of CNS cells have demonstrated that mature neurons, oligodendrocyte, and both type 1 and type 2 astrocytes express immunoreactive Reo3R but 0-2A progenitor cells do not.

A cell-surface structure utilized as an attachment site by reovirus type 3 appears at an early stage of oligodendrocyte development and is expressed on mature oligodendrocytes and astrocytes in culture. Addition of antibodies and peptides which specifically bind the Reo3R to neonatal rat optic nerve cultures stimulates expression of galactocerebroside (GalC) with increased numbers of GalC(+) cells. The Applicants' studies demonstrate that antibodies which recognize the Reo3R stimulate several additional features of oligodendrocyte differentiation. Addition of anti-Reo3R antibody to neonatal rat optic nerve cultures stimulates conversion of 0-2A progenitor cells into immature A2B5(+) GalC(+) oligodendrocyte within 24 hours. These cells subsequently differentiate into A2B5(−) GalC(+) MBP(+) cells. (MBP is myelin basic protein). GalC is first detected on cells having the appearance of immature oligodendrocyte, suggesting that Reo3R perturbation does not stimulate the morphological concomitants of myelin component biosynthesis.

Compounds bindable with the reovirus type 3 receptor stimulate oligodendrocyte differentiation and are expected to be useful in remyelination of nerve cells after myelin destruction such as occurs in multiple sclerosis and viral infection. The peptides and antibodies of the invention stimulate the appearance of components of myelin biosynthesis. The early appearance of the components of myelin biosynthesis should result in earlier remyelination of damaged nerves. Remyelination of damaged nerves should consequently lessen or reverse the neural deficits found in these conditions. As used herein the terms stimulation of myelin production, stimulation of myelin formation, stimulation of remyelination and similar terms include activity upon the biological processes whereby myelin is formed by transcription of myelin genes, and from precursor molecules. These terms may also include activity upon the processes of cellular differentiation of progenitor cells into mature oligodendrocytes, the biosynthesis of myelin-specific components, as well as the biological processes whereby the sheath that surrounds nerve axons is formed.

At the present time peptides and antibodies are preferred for use in the methods of the invention. However, other compounds bindable with the reovirus type 3 receptor on oligodendrocytes that stimulate the early appearance of the components of myelin biosynthesis are also within the scope of the invention. Suitable compounds may be obtained through the use of molecular modelling techniques and screening compounds for their ability to bind to the reovirus type 3 receptor and stimulate the appearance of the components of myelin biosynthesis. Suitable methods for screening compounds include the methods disclosed herein in the Examples for testing peptides, and binding compounds to cells expressing the reovirus type 3 receptor on the cell surface.

Antibodies useful in the methods of the invention may be prepared by standard techniques for preparing monoclonal antibodies. Antibodies bindable with the reovirus type 3 receptor expressed on the surface of oligodendrocytes may be prepared as anti-idiotype antibodies of the receptor or as anti-receptor antibodies. Anti-idiotype antibodies may be prepared by first preparing neutralizing antibodies to reovirus type 3 (i.e. antibodies specific for reovirus type 3 wherein the specificity of the antibody is such that the antibody when bound to a portion or epitope of the virus precludes the infection of cells by the virus). This may be done by the method of Burston et al. (1982) Virology 117: 146–155, the disclosures of which are hereby incorporated as if fully set forth herein. The neutralizing antibodies are then used to make anti-idiotype antibodies by immunizing a mammal such as a mouse with hybridoma cells Which secrete the neutralizing antibody and screening the resulting antibodies. This may be done by the method of Noseworthy et al., (1983) J. Immunol. 131:2533 the disclosures of which are hereby incorporated as if fully set forth herein.

Because antigens such as viruses generally contain multiple antigenic epitopes, it may be necessary to screen the antibodies produced in response to the inoculation with the ligand, receptor or anti-ligand antibody to select antibodies having specificity for the neutralizing epitope of the antigen. Screening can be done by competitive assays that determine the antibody's ability to inhibit binding of the antigen to the receptor of the cell, those antibodies having a greater ability to inhibit binding of the antigen containing or mimicking the neutralizing epitope. Suitable screening methods include those described herein, and in Burstin, S. J., et al., "Evidence For Functional Domains On The Reovirus Type 3", Hemagglutinin Virology 117:146–155. It will be obvious to those skilled in the art that various changes to reagents may need to be made in the competitive assays when different antigen and receptor pairs are used.

Instead of using an anti-receptor antibody that was produced as an anti-idiotype antibody, the receptor itself is also suitable for producing antibodies that have epitopes mimicking the antigen. To produce antibodies by this route, receptor bearing cells are used as an immunogen, as for example in Drebin, et al., "Monoclonal Antibodies Recognize A Cell Surface Antigen Associated With An Activated Cellular Oncogone", Nature (1984) 321:545-547 and Drebin, et al., "Down Modulation Of Oncogene Protein Expression And Reversion Of The Transformed Phenotype By Monoclonal Antibodies", Cell (1985) 41:695-706. Alternatively, purified receptor can be used, as for example in Nepom, et al., "Identification Of A Hemagglutinin Specific Idiotype Associated With Reovirus Recognition Shared By Lymphoid And Neuronal Cells", J. Exp. Med. (1982) 155:155-178 and Noseworthy, et al., "Cell Receptors For Mammalian Reovirus. I. Syngeneic Monoclonal AntiIdiotypic Antibody Identifies A Cell Surface Receptor For Reovirus", J. Immmanuel. (1983) 131:2533-2538. These two immunogens can be used to make antibodies, usually monoclonal antibodies, by conventional techniques. An animal such as a mouse is first injected with the receptor, its spleen cells are removed and fused with myeloma cells to form hybridoma cells, the latter are cloned in a serum-containing medium and the monoclonal antibodies are separated from the medium. The antibodies are then screened by neutralization assay, as described above, to select those antibodies which specifically bind to the receptor site at the neutralizing epitope.

Peptides useful in the invention are preferably synthetic peptides having a length of from about six to about seventy-five amino acid residues. In a preferred embodiment, the peptides are peptide dimers having first and second peptide sequences each sequence comprising an amino acid sequence bindable with the reovirus type 3 receptor. The first and second sequences preferably comprise the amino acid sequence Lys-Pro-Gly-Lys-Thr-Asn-Lys-Leu-Ile-Tyr-Ser-Gly-Ser-Thr-Leu-Gln or a derivative thereof bindable with the reovirus 3 receptor, wherein the dimer may comprise any combination of first and second peptide sequence, first peptide sequences or second peptide sequences. More preferably the first and second peptide sequences comprise the amino acid sequences Cys-Lys-Pro-Gly-Lys-Thr-Asn-Lys-Leu-Leu-Ile-Tyr-Ser-Gly-Ser-Thr-Leu-Gln, Cys-Lys-Pro-Gly-Lys-Thr-Asn-Lys-Leu-Leu-Ile-Phe-Ser-Gly-Ser-Thr-Leu-Gln, Cys-Lys-Pro-Gly-Lys-Thr-Asn-Lys-Leu-Leu-Ile-Tyr-Ala-Gly-Ser-Thr-Leu-Gln, Cys-Lys-Pro-Gly-Lys-Thr-Asn-Lys-Leu-Leu-Ile-Tyr-Ser-Ala-Ser-Thr-Leu-Gln, Cys-Lys-Pro-Gly-Lys-Thr-Asn-Lys-Leu-Leu-Ile-Tyr-Ser-Gly-Ser-Thr-Leu-Gln.

The peptides useful in the invention may be made by standard peptide synthesis techniques such as chemical synthesis and solid phase synthesis. The peptides may be dimerized by any convenient method, such as the method described herein. Briefly, are peptides synthesized to contain a terminal cysteine residue peptide and the peptides are dimerized by stirring a 5 mg/ml solution in 0.1M ammonium bicarbonate overnight at 23° C. exposed to air.

The peptides and antibodies useful in the invention are administered to a mammal, which will generally be a human, in combination with a pharmaceutically acceptable carrier or diluent such as water, saline or other buffer. The peptides and antibodies may also be combined with other delivery systems such as liposomes or conjugated to other compounds for delivery to the site of nerve injury. The antibodies and peptides may be administered by any convenient route, such as intravenous and oral administration. The antibodies and peptides may be administered for a length of time effective to stimulate oligodendrocyte differentiation, stimulate the appearance of the components of myelin biosynthesis, or until remyelination of damaged nerves has occurred. The length of time the peptides and antibodies may be administered will also depend on such factors as the condition being treated and the extent of nerve damage.

EXPERIMENTAL

SYNTHESIS OF PEPTIDES

Peptides were synthesized using a model 430A Applied Biosystems Peptide Synthesizer (Applied Biosystems, Inc., Foster City, Calif. Deprotection and release of the peptide from the solid phase support matrix were accomplished by treating the protected peptide on the resin with anhydrous HF containing 10% anisole or 10% thioanisole for 1 to 2 hr at 0 degrees C. The peptides were then extracted with either ethyl acetate or diethylether and then dissolved in 10% aqueous acetic acid and filtered to remove the resin. After lyophilization, the composition and purity of the peptides were determined with both amino acid analysis and reverse phase high performance liquid chromatography. This procedure was used for the synthesis of all peptides, including $V_L$ and the peptide derivatives of $V_L$.

$V_L$ peptide was synthesized with an additional amino terminal cysteine residue ($V_L$SH) to form a dimeric peptide. VL$_S$H peptide was dimerized by stirring a 5 mg/ml solution in 0.1M ammonium bicarbonate overnight at 23° C. exposed to air. The peptides were then lyophilized. Dimerization was confirmed by Ellman determination according to the procedure of Ellman, G. L. Arch. Biochem. Biophys. 74: 443 (1958), which revealed less than 5% free sulfhydryl groups.

Reo3R-binding peptides (Table 1) corresponding to the region of sequence shared by the reovirus $\sigma$1 protein and the monoclonal anti-Reo3R antibody, 87.92.6, were synthesized as described herein. Peptides were further purified by a gel filtration over a Sephadex G-25 column. Composition and purity were confirmed by amino acid analysis and reverse phase high performance liquid chromatography.

TABLE 1

| Reo3R-binding peptides | |
|---|---|
| Reovirus type 3 | Q S M — W I G I V S Y S G S G L N |
| $\sigma$1 protein | 317　　　　　　　　　　　　　　332 |
| $V_L$ peptide | K P G K T N K L L I Y S G S T L Q |
| $V_L$ SH peptide | C K P G K T N K L L I Y S G S T L Q |
| Peptide F | C N G S H V P D H D V T E E R D E |

The amino acid sequence of the Reo3R-binding region of the reovirus type 3 $\sigma$1 protein is listed. $V_L$ peptide corresponds to a region of nearly identical sequence present in the light chain CDR in of the 87.92.6 anti-Reo3R antibody. $V_L$SH peptide is the $V_L$ sequence plus an amino-terminal cysteine to allow dimerization. Peptide F is a control peptide with pI, net charge, and hydrophobicity approximately equal to that of $V_L$.

NEONATAL RAT OPTIC NERVE GLIAL CULTURE MODEL FOR STUDY OF MYELINATION

The neonatal rat Optic nerve glial culture system provides a useful model for the study of myelination. In this system, 0-2A glial progenitor cells have been identified which differentiate into oligodendrocyte and type 2 (fibrous) astrocytes. Type 1 (protoplasmic) astrocytes, also present in these cultures, probably arise from a separate lineage. Each of these cell types can be identified by morphological criteria and by the expression of characteristic surface and cytoplasmic antigens. 0-2A progenitors are motile cells with a simple bipolar morphology which react with the A2B5 antibody. Immature oligodendrocyte extend simple branching processes an react with both the A2B5 and 04 antibodies. As oligodendrocytes assume a more mature morphology with extensive branching processes, they lose A2B5 reactivity and express a variety of myelin-specific products including galactocerebroside (GalC), myelin basic protein (MBP), proteolipid protein (PLP), myelin-associated glycoprotein (MAG), and cyclic nucleotide phosphohydrolase (CNPase). Astrocytes can be identified by the expression of glial fibrillary acidic protein (GFAP) and lack of expression of GalC. Type 1 astrocytes have a flat triangular shape and A2B5(−) GFAP(+) phenotype. Type 2 astrocytes have long processes and A2B5(+) GFAP(+) phenotype.

Neonatal rat optic nerve glia were cultured according to the methods described by Raff et al. (1983) Nature 303: 390-396. Briefly, optic nerves were removed from rat pups on the day indicated and dissected free of chiasmal tissue and meninges. Single cell suspensions were prepared by mincing the nerves with microknives, digestion with collagenase and trypsin, and gentle trituration. $3 \times 10^3$ cells were plated on 12 mm glass coverslips in 24 well culture plates (Falcon, Becton Dickinson Labware, Lincoln Park, N.J.) in 25 µL Dulbecco's Modified Eagles Medium (Gibco Laboratories, Grand Island, N.Y.) supplemented with 10% heat-inactivated fetal calf serum (FCS, Hyclone Laboratories, Logan, Utah). Prior to use the coverslips were coated with polyL-lysine (MW=410 000, Sigma Chemical Co., St. Louis, MO). After 1 hour to allow the cells to attach, 475 µL of N2 medium (Bottstein, J. E. and Sate, G. H. (1979) Pro.Natl.Acad.Sci USA 76: 514-517) as modified by Raff et al. (1983) Nature 303: 390-396 was added, bringing the final serum concentration to 0.5% (N2/0.5% FCS).

ANTIBODIES

The isolation and characterization of the anti-Reo3R antibodies, anti-ID3 (13) and 87.92.6 (24), are described in Nepom et al. (1982) J. Exp. Med. 155:155-167, and Drayna, D. and Fields, B. N. (1982) J. Gen. Virol. 63:149-159, respectively. The mouse A2B5 monoclonal antibody specific for GQ ganglioside (Eisenbarth, G.S. et al. (1979) Proc.Natl.Acad.Sci USA 76: 4913-1300) was obtained from the American Type Culture Collection (accession number CRL 1520). The mouse 04 monoclonal antibody (Schacnher, M. et al. (1981) Devel.Biol. 311-327) Was provided by Dr. M. Schachner, E. T. H., Zurich Mouse monoclonal anti-GalC antibody (Ranscht, B. et al. (1982) Proc.Natl.Acad.Sci U.S.A. 79: 2709-2713) was provided by Dr. B. Ranscht, La Jolla Cancer Research Center, La Jolla, Calif. The rat monoclonal antibody specific for MBP, MID3, was provided by Dr. W. Hickey, Washington Univ., St. Louis, Mo. 2.2B 10.6, a rat monoclonal antibody specific for GFAP (Lee, V. M.-Y. et al. (1984) J. Neurochem 42:25-32) was provided by D.r V. Lee, Univ. of Penn., Philadelphia, Pa. H013.4 and H022.1, mouse IgM monoclonal antibodies specific for mouse Thy 1.2 and Thy 1.1 were obtained from the American Type Culture Collection (accession numbers TIB 99 and TIB 100, respectively). All fluorochrome-conjugated secondary antibodies were purchased from Tago, Burlingame, Calif.

For immunocytochemical studies, antibodies were used at a saturating dilution of concentrated culture supernatant of clarified ascites. Antibodies used to treat developing glial cultures were further purified. The mouse IgM monoclonal antibodies 87.92.6, H013.4, and H022.1 were purified from clarified mouse ascites by adsorption to anti-mouseµ—agarose (Sigma) columns and elution with 3.5 M MgClz. Anti-ID3 IgG was prepared from rabbit antiserum by ammonium sulfate precipitation and passage over a Protein A - Sepharose CL-4B (Sigma) column. The purfied antibodies were dialyzed extensively against phosphate buffered saline, concentrated by ultrafiltration, filter sterilized, and stores at −70° C. until use. Protein concentration was determined by absorbance at 280 nm. Purity was confirmed by SDS-PAGE electrophoresis.

IMMUNOCYTOCHEMICAL STUDIES

To double label for Reo3R and other qlial differentiation markers, the cells were fixed with 2% paraformaldehyde in Hanks balanced salt solution (HBSS) for 5 minutes at 4° C. Antibody dilutions and subsequent washes were performed in HBSS supplemented with 10 mM HEPES, 4% FCS, and 0.2% $NaN_3$ (IFM buffer). The cells were incubated successively in 50 µg/ml anti-ID3 followed by goat anti-rabbit IgG-rhodamine for 30 minutes each at room temperature. They were then incubated for 30 minutes at room temperature with saturating concentrations of A2B5, 04, anti-GalC, MID3, or 2.2B10.6 followed by FITC-conjugated goat secondary antibody for the appropriate specificity. Prior to staining for MBP with M2D3, the cells were permeabilized by incubation in acetone at room temperature for 10 minutes. Prior to staining for GFAP with 2.2BIO.6, the cells were permeabilized with 5% glacial acetic acid in ethanol for 5 minutes at −20° C. After immunostaining, the coverslips were post-fixed in 5% glacial acetic acid in ethanol for 5 minutes at −20° C. and mounted in glycerol/PBS containing 0.2M DABCO (Johnson et al. (1982) J. Immunol. Meth. 55: 231-242). The coverslips were examined using a Leitz Dialux 20 microscope equipped for phase contrast and epifluorescence microscopy.

To double label for A2B5 and GalC or 04 and GalC, the cells were fixed with 2% paraformaldehyde in HBSS for 5 minutes at 4 ©C. They were then incubated successively in saturating concentrations of anti-GalC antibody, goat anti-mouse IgG—FITC, A2B5 or 04 antibody, and goat anti-mouse IgM—Rhodamine (µchain specific) for 30 minutes each at room temperature.

Prior to incubation with MID3, the cells were permeabilized by incubation in acetone at room temperature for 10 minutes. Prior to incubation with 2.2B10.6, the cells were permeabilized with 5% glacial acetic acid in ethanol for 5 minutes at −20° C.

VIRUS BINDING STUDIES

Reovirus types and 1 and 3 (kindly provided by Dr. D. H. Rubin, Univ. of Penn.) were grown on murine L cells and purified by CsCl gradient centrifugation according to the method in Ramig et al. (1977) J. Virol. 22:726–733, or Drayna, D. and Fields, B. N. (1982) J. Gen. Virol. 63:149–159. Coverslips were incubated in 100 μL IFM buffer containing $10^8$ a type 1 or 3 viral particles at 4° C. for 1 hour. After washing, the coverslips were incubated for 30 minutes each in rabbit reovirus-specific antiserum followed by goat anti-rabbit IgG-FTC. The rabbit reovirus-specific antiserum was prepared according to the method in Weiner, et al. (1988) Microbiol. Path. 5:29–40) The cells were then double labelled for the glial markers (A2B5, 04, GalC, MBP, or GFAP) as described above.

DETERMINATION OF PRELIFERATION BY IMMUNOSTAINING FOR BRDU INCORPORATION

To determine the effect of anti-Reo3R antibody on cellular proliferation, the proportion of cells in the 0-2A lineage undergoing mitosis in culture was determined by the method of Yong and Kim (1987) J. Neurosci. Meth. 9–16 with the following adaptations. Glial cultures were cultured for 24 hours in N2/0.5% FCS containing 10 uM bromodeoxyuridine (BrdU) (Sigma) plus anti-Reo3R or control antibody. At the end of the culture period, the medium was replaced with fresh medium without BrdU and the cells incubated for an additional 30 minutes. The cells were fixed in 2% paraformaldehyde in HBSS for 5 minutes at 4° C. then stained with A2B5 followed by goat anti-mouse IgM-rhodamine or anti-GalC followed by goat anti-mouse IgG-rhodamine. The cells were permeabilized with 70% ethanol for 30 minutes at $-20°$ C., then incubated in 2N HCl at room temperature for 10 minutes followed by 0.1M sodium borate at room temperature for 10 minutes. The coverslips were incubated sequentially in anti-BrdU antibody (Becton Dickinson) diluted 1/10 followed by goat anti-mouse IgG-FITC. The coverslips were mounted and examined as described above. Despite the additional surface staining resulting from reactivity of goat anti-mouse IgG-FITC with bound A2B5 and anti-GalC, this was easily distinguished from the nuclear staining reflecting BrdU incorporation.

MITOMYCIN C TREATMENT

A stock solution of 0.5 mg/ml mitomycin C (Sigma) in HBSS (Gibco) was prepared and stored at 4° C. in the dark. Cultures were treated with 25 μg/ml mitomycin C diluted in N2 / 0.5% FCS for 30 minutes at 37° C. in the dark. The cultures were washed twice with N2/0.5% FCS and cultured for an additional 24 or 48 hours.

STATISTICAL ANALYSIS

Sample means were compared using a paired T-test for populations with unknown, unequal variance or analysis of variance according to the method in Dixon, W. J. and Massey, F. J. (1969) Introduction to Statistical Analysis, McGraw-Hill Book Company, New York, N.Y.

RESULTS

NORMAL DEVELOPMENT SEQUENCE IN OPTIC NERVE CULTURES

To allow detection of potentially subtle changes induced by Reo3R-binding ligands, it was necessary to carefully characterize the timecourse of oligodendrocyte differentiation in the neonatal rat optic nerve culture system. Single cell suspensions were prepared from neonatal rat optic nerves on a postnatal day 1 (PND-1) or PND-4 as described in Experimental Methods. $3 \times 10^3$ cells were plated on poly-L-lysine-coated coverslips in N2 medium containing 0.5% FCS (N2/0.5% FCS). After 1, 2, 4, or 7 days of culture, the cells were double immunostained for A2B5 and GalC, 04 and GalC, GalC and MBP, or A2B5 and GFAP.

The predominant cell in these cultures was the type 2 astrocyte, characterized by a flat triangular shape and expression of GFAP but neither A2B5 nor GalC. The absolute and relative numbers of these cells increased over time. Cells for the 0-2A lineage were present in smaller numbers but comprised the majority of the remaining cells.

The phenotypic profile of cells in the 0-2A lineage rapidly evolved in cultures prepared on PND-1. Initially, A2B5(+) GalC(−)progenitor cells with a simple bipolar morphology represented the most common cells of the 0-2A lineage. The number of these cells was markedly decreased by day 2. By day 4 these cells were virtually absent.

The 04 marker has ben reported to appear at an early stage of oligodendrocyte development prior to the appearance of GalC (6). On days 1 and 2 of culture substantial numbers of 04(+) GalC(−) cells with short, simple processes with a small number o branches were also present. These cells subsequently decreased in number. Small numbers of GalC(+) oligodendrocyte were present on day 1 of culture. These cells uniformly expressed A2B5 and 04 and exhibited long processes With multiple branches. The absolute number of A2B5(+) GalC(+) cells increased until day 2 or 3 of culture then decreased as the cells further differentiated and ceased to express A2B5. Mature A2B5(−) GalC(+) oligodendrocyte with extensive, complex branching processes were rare or absent before day 2–3 of culture. The number of such cells steadily increased up to day 4. No further increase was observed on day 7. The number of 04(+) GalC(+) cells were virtually identical, suggesting that these two cell populations were the same. Similar results were obtained in studies of cultures set up on PND-4, aside from the earlier appearance of mature oligodendrocyte.

In 4 separate experiments, cells expressing immunoreactive MBP were first detected in cultures initiated on PND-1 after 7 to 8 days of culture. In cultures set up on PND-4 (3 separate experiments), MBP(+) cells appeared after 3 or 4 days. Thus, MBP appeared on the equivalent of PND-7 to 8 regardless of the day of culture. MBP(+) cells were uniformly GalC(+). Prior to PND-7 no GalC(+) cells expressed MBP. Subsequently, the proportion of GalC(+) cells which also expressed MBP progressively increased. These results agree with previous studies (2, 6, 28 31) suggesting that cells of the 0-2A lineage sequentially express the following antigenic phenotypes: A2B5(+) 04(−) GalC MBP(−)→A2B5(+)  04(+)  GalC(−) MBP(−)→A2B5(+)  04(+)  GalC(+)

MBP(−)→A2B5(−) 04(+) GalC(+)
MBP(−)→A2B5(−) 04(÷) GalC(+) MBP(+).

In cultures maintained in N2/0.5% FCS, type 2 astrocytes, characterized by long simple processes an the A2B5(+) GalC(−) GFAP(+) phenotype, were observed infrequently. These cells typically appeared on the equivalent of PND-7 to 10.

EXPRESSION PATTERN OF REO3R DURING OPTIC NERVE OLIGODENDROCYTE DIFFERENTIATION

Previous studies demonstrated that immunoreactive Reo3R is expressed by mature oligodendrocyte and both type 2 and type 2 astrocytes in culture but not by 0-2A progenitor cells (Ventimiglia, R. et al. (1987) Proc.Natl.Acad.Sci. USA 84: 5073-5077. To determine the timing of appearance of the Reo3R more precisely, optic nerve cultures were set up on PND-1 (2 experiments) or PND-4 (2 experiments). Coverslips were removed over the next 4 days and double immunostained for Reo3R and for A2B5, 04, GalC, MBP, or GFAP. The results of a representative experiment are presented in Table 2. The values represent the percentage of Reo3R(+) cells among cells expressing each glial marker. The fractions in parentheses represent actual cell counts from an individual coverslip. The denominators represent the total number of cells expressing a given glial marker. The numerators represent the numbers of such cells which also expressed Reo3R.

TABLE 2

| | Expression of the Reo3R during oligodendrocyte differentiation | | | | |
|---|---|---|---|---|---|
| Days in Culture | Percentage of Cells Expressing Reo3R Among Cells Expressing Other Glial Markers | | | | |
| | GFAP | A1B5 | O4 | GalC | MBP |
| 1 | 71.7 | 5.5 | 51.7 | 93.1 | |
| | (607/847) | (13/236) | (611 118) | (27/29) | (0/0) |
| 2 | 92.7 | 31.2 | 29.9 | 88.8 | |
| | (1124/1213) | (39/125) | (47/157) | (1741 196) | (0/0 |
| 4 | 96.9 | 25.0 | 46.6 | 92.9 | 100 |
| | (1648/1701) | (2/8) | (125/268) | (223/240) | (12/12) |

As noted above, type 1 astrocytes were the most numerous cells in these cultures. The relative numbers of these cells progressively increased as did the proportion expressing immunoreactive Reo3R. After four days in culture, 96-98% expressed the Reo3R.

A2B5(+) cells were numerous on day 1 of culture; the majority were bipolar or exhibited short simple processes typical of 0-2A progenitor cells. These cells were uniformly negative for Reo3R. The A2B5(+) Reo3R(+) cells observed particularly on days 2 and 3 of culture represented early oligodendrocyte, as evidenced by their weak A2B5(+) reactivity and relatively complex processes. At early timepoints, few cells expressed the 04 marker. The number of 04(+) cells increased progressively over the four day culture period. At all timepoints, one third to one half of the 04(+) cells expressed Reo3R. Mature oligodendrocytes, expressing GalC followed by MBP, were rare at the outset of culture. Their number increased over four days. Virtually all of the GalC(+) and MBP(+) cells expressed Reo3R.

Reovirus type 3 binding studies demonstrated a developmental expression pattern identical to that obtained with anti-Reo3R antibody. Reovirus type 1 did not bind to glial progenitors or to mature astrocytes or oligodendrocyte. When cultures were double labelled using reovirus type 3 and anti-Reo3R antibody binding (nonsaturating concentrations of both), identical cell populations were stained. These results confirm earlier studies showing that the anti-Reo3R antibodies identify a binding site for reovirus type 3 expressed by CNS glia.

STIMULATION OF GALC EXPRESSION BY ANTI-REO3R ANTIBODIES

Because of the developmentally regulated expression pattern of the Reo3R during oligodendrocyte differentiation and because of the biochemical and antigenic similarity of the Reo3R to the $\beta$-adrenergic receptor ($\beta_2$AR), the effects of perturbation of the Reo3R on oligodendrocyte development were tested. To determine the effects of perturbation of the Reo3 receptor on oligodendrocyte development, $3 \times 10^3$ cells isolated from neonatal rat optic nerves on PND-1 were cultured in N2 medium/0.5% FCS alone or with varying concentrations of purified 87.92.6 anti-Reo3R antibody. In 7 separate experiments, the addition of 87.92.6 to the cultures at concentrations of 1-50 µg/ml stimulated GalC expression leading to increased numbers of GalC(+) cells within 24 hours.

Polyclonal anti-Reo3R antiserum, anti-ID3, also stimulated GalC expression. The weaker effect of this antiserum relative to 87.92.6 may reflect its polyclonal nature and a smaller proportion of antibody molecules which bind the Reo3R. µg/ml HO 13.4 or H022.1, isotype-matched (IgM) cOntrol antibodies purified in parallel in a manner identical to that of 87.92.6, was no different from cultures containing N2/0.5% FCS alone.

To further demonstrate the specificity of the effect of anti-Reo3R antibody on GalC expression, the antigen binding domain of 87.92.6 was blocked prior to addition to the cultures. Pre-incubation with purified 9B.G5, the anti-type 3 $\sigma$1 antibody used to generate 87.92.6 (14), abrogated the ability of anti-Reo3R antibody to stimulate GalC expression. Finally, 50 µg/ml purified normal rabbit immunoglobulin produced no change in the expression of GalC.

The induction of GalC expression occurred rapidly. A substantial increase in the number of GalC(+) cells was observed after 24 hours of culture in the presence of 10 µg/ml 87.92.6. At this early timepoint the predominant effect represented an increase in the number of A2B5(+) GalC(+) cells. Initially, these cells were strongly A2B5 positive. After two days of culture, the number of A2B5(+) GalC(+) cells remained higher in cultures treated with anti-Reo3R antibody relative to control cultures. However, in some experiments, this difference was no longer statistically significant. By day 3 of culture, the number of A2B5(+) GalC(+) cells in cultures treated with anti-Reo3R antibody began to decrease, reflecting further differentiation of these cells with loss of A2B5 reactivity.

After one day of culture there was a small but consistent and statistically significant increase in the number of A2B5(−) GalC(+) cells in cultures treated with 87.92.6 relative to cultures containing control antibody. By day 2 of culture there were substantially greater numbers of these cells in cultures containing anti-Reo3R antibody. This difference was even more pronounced by day 3. By day 5 of culture the numbers of A2B5(−) GalC(+) cells in treated and control cultures were equal. Thus, anti-Reo3R antibody induced early GalC expression in immature cells, manifested as an increased numbers of A2B5(+) GalC(+) cells after one day of culture. Anti-Reo3R antibody also stimulated loss of A2B5 reactivity leading to increased numbers of A2B5(−) GalC(+) cells during the first 4 days in culture. Kinetics of Antibody-mediated Induction of GalC Expression Previous studies of clonal cell lines have shown that maximal Reo3R-mediated inhibition of proliferation occurs rapidly and requires incubation with anti-Reo3R antibody for only one hour (Gaulton, G.N. and Greene, M.I. (1989) J. Exp. Med. 169: 197–211) Therefore, studies were undertaken to determine the length of treatment necessary for maximal stimulation of GalC expression in neonatal rat optic nerve cultures. 50 μg/ml 87.92.6 antibody was added to PND-1 optic nerve cultures immediately after the cells were observed to be attached to the coverslip. After incubation at 37° C. for varying lengths of time, bound antibody was removed by a 1 minute wash with DMEM containing 25 mM sodium acetate (pH=4.0). The cultures were washed several times with fresh N2/0.5% FCS and cultured for a total of 48 hours. Induction of the maximal number of cells expressing GalC at 48 hours required treatment of the cultures for 6–12 hours. No additional effect was observed by continued treatment for 24 hours or for the entire 48 hour culture period.

We hypothesized that requirement for a 6–12 hour incubation with anti-Reo3R to induce maximal GalC expression in cultures treated immediately after plating, may have resulted, in part, from the time required for Reo3R appearance on a substantial proportion of cells of the 0-2A lineage. To test this hypothesis treatment was delayed until after 24 hours of culture. In this case, incubation with anti-Reo3R antibody for 4 hours produced a maximal effect.

STIMULATION OF GALC EXPRESSION BY REO3R-BINDING PEPTIDES

To molecularly define the structural features of Reo3R ligands necessary for modulation of oligodendrocyte differentiation, synthetic peptides corresponding to the receptor-binding regions of the reovirus type 3 μ1 protein and the anti-Reo3R antibody, 87.92.6, were utilized. The sequences of these peptides are listed in Table 1. To produce a divalent Reo3R-binding peptide capable of crosslinking Reo3R molecules on the cell surface, an amino-terminal cysteine residue was added to the $V_L$ sequence. The resultant peptide, designated $V_L SH$, was dimerized as described in Williams et al. (1988) Proc. Natl. Acad. Sci. U.S.A. 85: 6488–6492.

Like intact anti-Reo3R antibody, the divalent Reo3R-binding peptide $V_L SH$ induced premature appearance of GalC when added to PND-1 optic nerve cultures at concentrations as low as 50 μg/ml. Peptide F, a control peptide with similar pI, net charge, and solubility characteristics, was ineffective. Monomeric $V_L$ peptide, which binds but does not crosslink Reo3R molecules did not induce GalC expression.

DISSOCIATION OF PHENOTYPIC FROM MORPHOLOGICAL MATURATION

In control cultures, the first cells observed to express surface GalC were weakly A2B5(+) and exhibited long processes with multiple branches. In contrast, after 24 hours of culture in the presence of anti-Reo3R antibody, a large proportion of GalC(+) cells had the antigenic phenotype and morphological appearance of immature oligodendrocyte. These cells reacted strongly with A2B5 antibody and exhibited short, simple processes. Lack of staining with a variety of isotype-matched control antibodies confirmed that the reactivity with anti-GalC antibody was specific. When left in culture for several additional days, these cells extended processes indistinguishable from those of normal oligodendrocyte in culture, arguing that the simple processes exhibited by the early appearing GalC(+) cells did not merely reflect a toxic effect of anti-Reo3R antibody. Rather, this finding suggests that these cells expressed GalC prematurely relative to their state of morphological maturation.

INDUCTION OF MBP

A later appearing myelin-specific gene product, MBP, also was induced in an accelerated manner by anti-Reo3R antibody. In two experiments, when $6 \times 10^3$ cells from PND-4 rat pups were cultured in N2/0.5% FCS plus 10 μg/ml 87.92.6 anti-Reo3R antibody, the early appearance of MBP relative to cultures with control antibody was observed. In both experiments MBP(+) cells were first detected in anti-Reo3R antibody-treated cultures on day 3 (equivalent to PND-7). Substantial numbers of MBP(+) cells were observed after the fourth day of culture. In contrast, only rare MBP(+) cells were detected in control cultures on day 4. By day 7 of culture the numbers of MBP(+) cells in the treated and control cultures were equal. Under both culture conditions, immunoreactive MBP was initially confined to the cytoplasm. When were maintained for several additional days, MBP also was detected in the oligodendrocyte processes.

DIRECTION OF GLIAL DIFFERENTIATION

Anti-Reo3R antibody did not appear to alter the path of glial differentiation. When added to optic nerve cultures set up on PND-4 and grown in N2 medium containing either 0.5% or 10% FCS, no difference in the number of process-bearing type 2 astrocytes expressing the A2B5 GFAP(+) phenotype was observed after either 48 or 96 hours of culture. In addition, no increase in the number of GalC(+) GFAP(+) cells occurred at either timepoint.

LACK OF EFFECT ON 0-2A PROLIFERATION

The onset of differentiation and expression of myelin markers is associated with the cessation of 0-2A cell proliferation. To test for an effect of Reo3R ligands on proliferation, cells were labelled over the first 24 hours of culture with BrdU in the presence of anti-Reo3R or control antibody. After 24 hours of culture the coverslips were double immunostained for BrdU incorporation and for A2B5 or GalC to determine the proportion of cells expressing these markers which had undergone cell division over the preceding day. In 3 separate experiments, 2–5% of both the A2B5(+) and the GalC(+) cells exhibited nuclear staining for BrdU in both the 87.92.6 and HO13.4- treated cultures. This proportion agrees with previous estimates of the mitotic index of 0-2A cells cultured in N2/0.5% FCS (Raff et al., (1983) Nature 303: 390–396; Noble and Murray, (1984) EMBO J. 3:2243–2247; Raff et al., (1985) Cell 42: 61–69; Richardson et al. (1988) Cell 53: 309–319) and confirms the rapidity with which cells of the 0-2A lineage drop out of the mitotic pool when placed in culture in N2 medium with low serum. No difference between the proliferative rates of control and anti-Reo3R antibody-treated cultures could be discerned. Given the low level of BrdU incorporation, further inhibition of proliferation would be difficult to detect. More importantly, no increase in the number of cells incorporating BrdU was observed. Thus, the increased number of GalC(+) oligodendrocyte observed in cultures treated with anti-Reo3R antibody did not result from a mitogenic effect leading to expansion of the precursor pool.

To test whether inhibition of proliferation per se affected the timing of GalC(+) appearance, optic nerve cultures prepared on PND-1 were treated with mitomycin C. After plating, the cells were incubated with 25 μg/ml mitomycin C for 30 minutes. After washing, the cultures were carried for an additional 24 or 48 hours. Decreased numbers of A2B5(+) cells were observed at both timepoints without a concomitant increase in the proportion of GalC(+) cells. These data suggest that Reo3R-perturbation alters oligodendrocyte differentiation independent of effects on cellular proliferation.

DISCUSSION

These studies demonstrate that a cell-surface structure utilized as an attachment site by reovirus type 3, although not expressed by glial progenitor cells, appears at an early stage of oligodendrocyte development and is expressed on virtually all mature oligodendrocyte and astrocytes in culture. Antibodies and peptides which bind the Reo3R stimulate GalC expression by developing oligodendrocytes. The differences between the control cultures and cultures treated with Reo3R ligands are significant. The stimulation of GalC expression represents a 200 to 400% increase in the number of GalC(+) cells. In this culture system, differences in the timing of appearance this marker of 1 to 2 days represent a substantial effect. Finally, these ligands are unique in their effect on oligodendrocyte differentiation.

A cell-surface structure utilized as an attachment site by reovirus type 3 appears at an early stage of oligodendrocyte development and is expressed on mature oligodendrocyte and astrocytes in culture. Addition of antibodies and peptides which specifically bind the Reo3R to neonatal rat optic nerve cultures stimulates expression of GalC with increased numbers of GalC(+) cells. The present studies demonstrate that antibodies which recognize the Reo3R stimulate several additional features of oligodendrocyte differentiation. Addition of anti-Reo3R antibody to neonatal rat optic nerve cultures stimulates conversion of 0-2A progenitor cells into immature A2B5(+) GalC(+) oligodendrocyte within 24 hours. These cells subsequently differentiate into A2B5(−) GalC(+) MBP(+) cells. GalC is first detected on cells having the appearance of immature oligodendrocyte, suggesting that Reo3R perturbation does not stimulate the morphological concomitants of myelin component biosynthesis. Alternatively, the rate at which oligodendrocyte can extend processes may be relatively fixed.

When cultured in defined medium, 0-2A progenitor cells rapidly cease dividing and differentiate into oligodendrocyte or type-2 astrocytes. This phenomenon can be reversed by supplementation of the culture medium with platelet-derived growth factor (PDGF), a potent mitogen for 0-2A progenitor cells, or by plating the cells on a bed layer of type-1 astrocytes In the presence of PDGF, 0-2A cells more gradually drop out of the mitotic pool and differentiate, analogous to their behavior in vivo.

These findings suggest several possible mechanisms for Reo3R-mediated stimulation of oligodendrocyte differentiation. Reo3R(+) type-1 astrocytes comprised the most abundant cells in the cultures employed in the present studies. The binding of Reo3R ligands may inhibit PDGF production by these cells, affecting oligodendrocyte differentiation indirectly. Reo3R ligands may compete with PDGF for its receptor (PDGF-R). Reo3R perturbation may decrease responsiveness to PDCF via receptor-receptor interaction or biochemical alteration of the PDGF-R at the membrane. Finally, Reo3R perturbation may decrease expression of PDGF-R.

We claim:

1. A method of inducing myelin formation by myelin forming cells expressing reovirus type 3 receptors comprising administering to such cells an effective amount of a peptide dimer having first and second peptide sequences, wherein said first and second peptide sequences are independently selected from Cys-Lys-Pro-Gly-Lys-Thr-Asn-Lys-Leu-Leu-Ile-Tyr-Ser-Gly-Ser-Thr-Leu-Gln, Cys-Lys-Pro-Gly-Lys-Thr-Asn-Lys-Leu-Leu-Ile-Phe-Ser-Gly-Ser-Thr-Leu-Gln, Cys-Lys-Pro-Gly-Lys-Thr-Asn-Lys-Leu-Leu-Ile-Phe-Ser-Gly-Ser-Thr-Leu-Gln, Cys-Lys-Pro-Gly-Lys-Thr-Asn-Lys-Leu-Leu-Ile-Phe-Ser-Gly-Ser-Thr-Leu-Gln, Syc-Lys-Pro-Gly-Lys-Thr-Asn-Lys-Leu-Leu-Ile-Phe-Ser-Gly-Ser-Thr-Leu-Gln.

2. A method of inducing oligodendrocyte differentiation comprising administering to such cells an effective amount of a peptide dimer having first and second peptide sequences, wherein said first and second peptide sequences are independently selected from Cys-Lys-Pro-Gly-Lys-Thr-Asn-Lys-Leu-Ile-Tyr-Ser-Gly-Ser-Thr-Leu-Gln, Cys-Lys-Pro-Gly-Lys-Thr-Asn-Lys-Leu-Ile-Tyr-Ser-Gly-Ser-Thr-Leu-Gly, Cys-Lys-Pro-Gly-Lys-Thr-Asn-Lys-Leu-Ile-Tyr-Ser-Gly-Ser-Thr-Leu-Gly, Cys-Lys-Pro-Gly-Lys-Thr-Asn-Lys-Leu-Ile-Tyr-Ser-Gly-Ser-Thr-Leu-Gly, Cys-Lys-Pro-Gly-Lys-Thr-Asn-Lys-Leu-Ile-Tyr-Ser-Gly-Ser-Thr-Leu-Gly.

3. The method of claim 1 wherein said first peptide sequence and said second peptide sequence are each Cys-Lys-Pro-Gly-Lys-Thr-Asn-Lys-Leu-Leu-Ile-Tyr-Ser-Gly-Ser-Thr-Leu-Gln.

4. The method of claim 2 wherein said first peptide sequence and said second peptide sequence are each Cys-Lys-Pro-Gly-Lys-Thr-Asn-Lys-Leu-Leu-Ile-Tyr-Ser-Gly-Ser-thr-Leu-Gln.

* * * * *